United States Patent [19]
Naves et al.

[11] Patent Number: 5,395,313
[45] Date of Patent: Mar. 7, 1995

[54] RECIPROCATING ARTHROSCOPIC SHAVER

[76] Inventors: Neil H. Naves, 28852 Woodcreek, Mission Viejo, Calif. 92692; Mark J. Legome, 3255 Driza, Mission Viejo, Calif. 92692

[21] Appl. No.: 236,657
[22] Filed: Apr. 29, 1994

Related U.S. Application Data

[63] Continuation of Ser. No. 106,275, Aug. 13, 1993, abandoned.

[51] Int. Cl.⁶ .............................................. A61B 17/20
[52] U.S. Cl. ..................................... 604/22; 128/751; 128/754
[58] Field of Search ................... 604/22; 128/751, 754

[56] References Cited

U.S. PATENT DOCUMENTS

| | | |
|---|---|---|
| 3,640,280 | 2/1972 | Slanker et al. |
| 4,011,869 | 3/1977 | Seiler, Jr. |
| 4,111,207 | 9/1978 | Seiler, Jr. |
| 4,210,146 | 7/1980 | Banko |
| 4,589,414 | 5/1986 | Yoshida et al. |
| 4,603,694 | 8/1986 | Wheeler ................ 604/22 |
| 4,644,951 | 2/1987 | Bays ...................... 604/22 |
| 4,662,376 | 5/1987 | Belanger ............... 604/22 |
| 4,662,869 | 5/1987 | Wright .................. 604/22 |
| 4,674,502 | 6/1987 | Imonti ................... 606/177 |
| 4,678,459 | 7/1987 | Onik et al. ............ 604/22 |
| 4,696,298 | 9/1987 | Higgins et al. ........ 604/22 |
| 4,867,157 | 9/1989 | McGurk-Burleson et al. |
| 4,961,430 | 10/1990 | Sheahon ................ 606/171 |
| 4,983,179 | 1/1991 | Sjostrom |
| 5,007,917 | 4/1991 | Evans |

FOREIGN PATENT DOCUMENTS 3447681 11/1985 Germany.

Primary Examiner—C. Fred Rosenbaum
Assistant Examiner—Perry E. Van Over
Attorney, Agent, or Firm—Knobbe, Martens, Olson & Bear

[57] ABSTRACT

An arthroscopic shaving device is disclosed which performs cutting by means of reciprocal motion of the cutting blade. The device comprises a long, hollow, tubular housing which houses a cutting member. The housing has an angled portion at its distal end which facilitates access to hard to reach spots such as the rear portion of a knee joint. The cutting member is reciprocated within the distal end of the housing and an aperture having a cutting edge is located within the cutting stroke of the cutting member so that cutting of soft tissue may be achieved at the distal end of the housing. The shaver may be embodied in two main configurations: a side-cutting configuration wherein the cutting aperture is located within the side of the tubular housing, and an end-cutting embodiment wherein the cutting aperture is located at the distal tip of the housing. Adaptations of the side-cutting embodiment include an embodiment wherein cutting is effected in the proximal direction and an embodiment wherein cutting is effected in the distal direction.

18 Claims, 11 Drawing Sheets

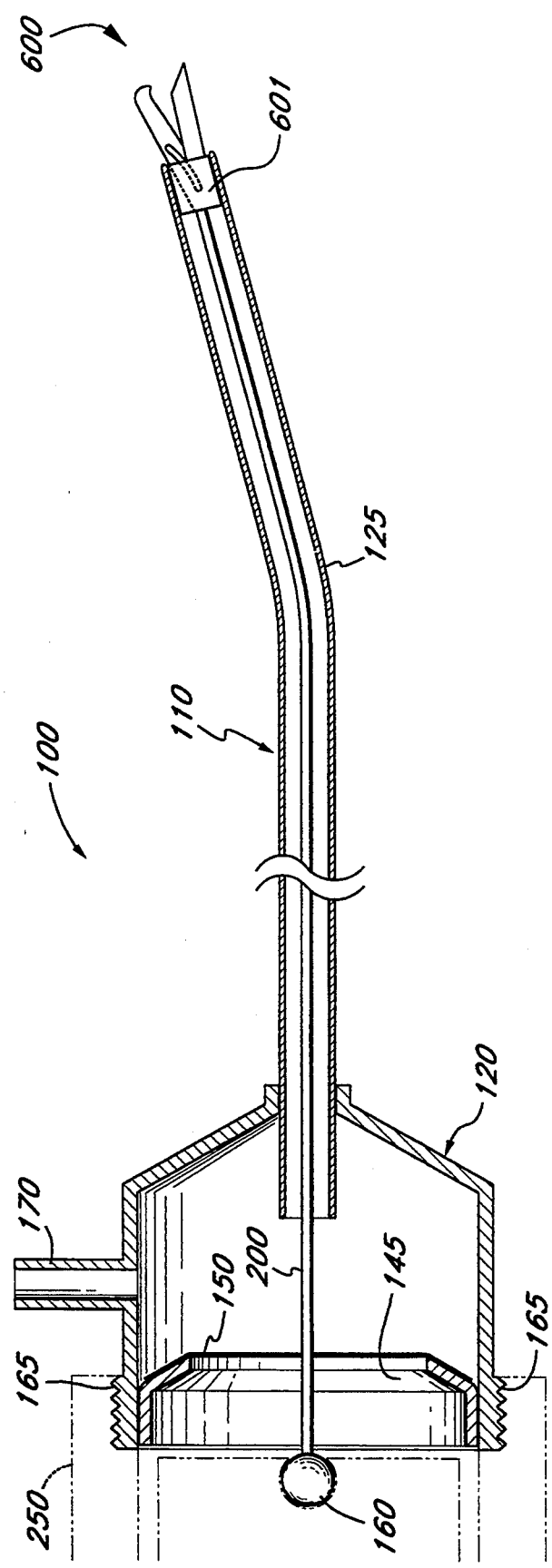

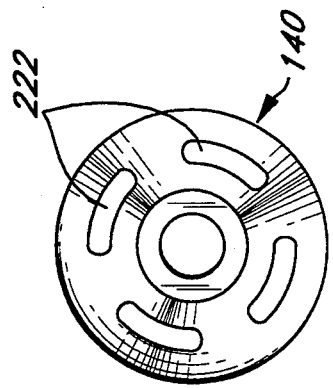
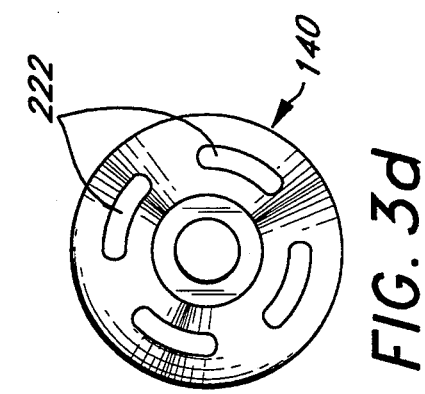
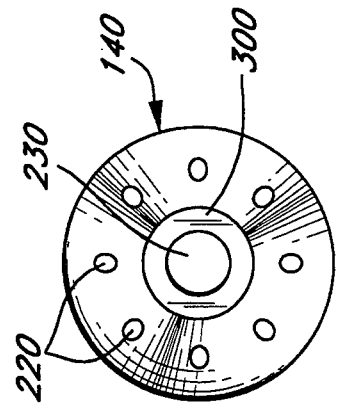
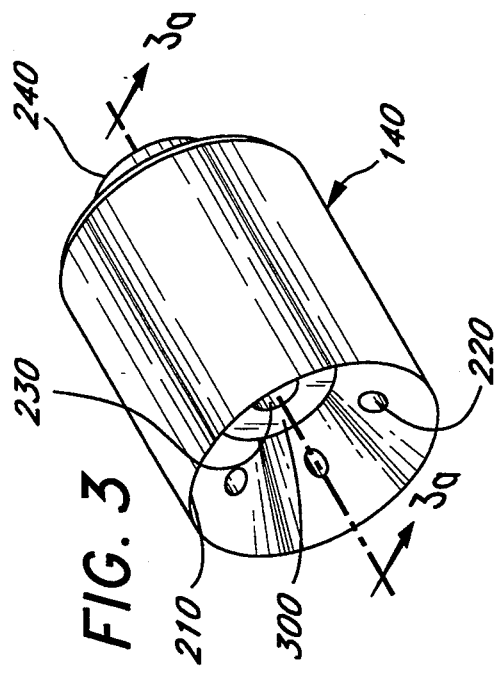
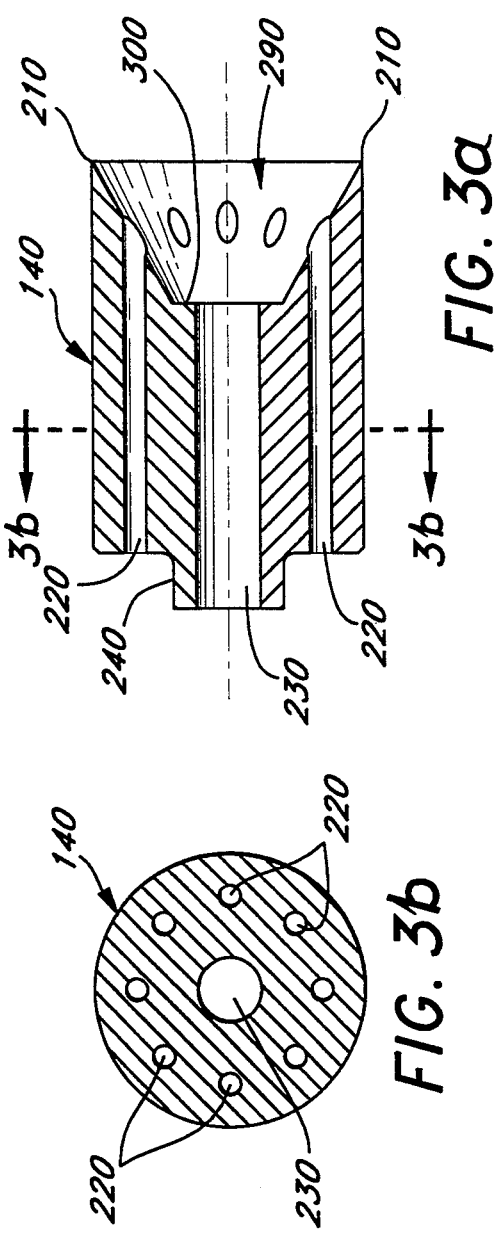

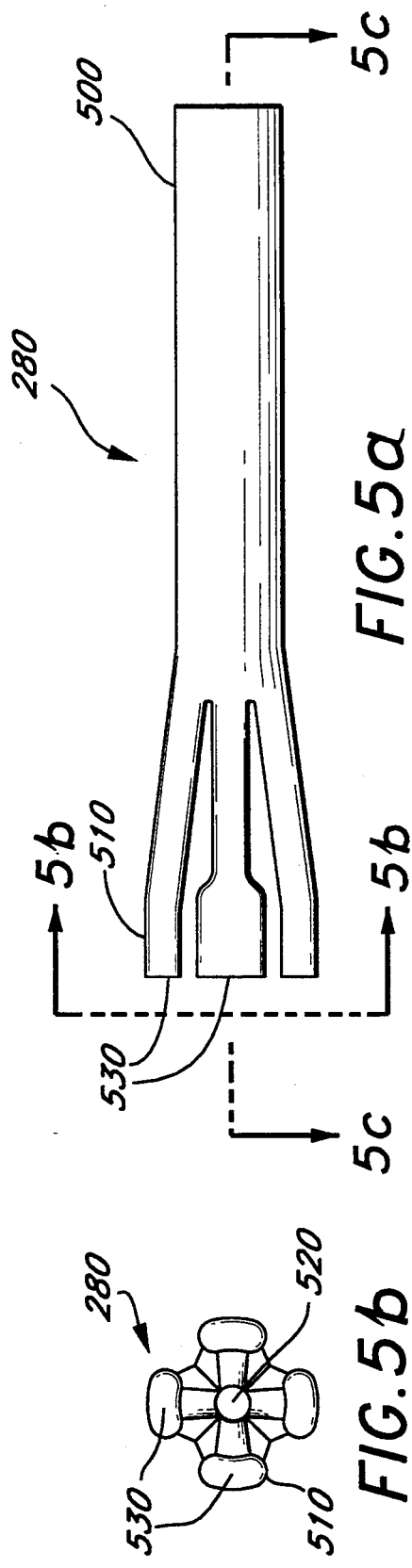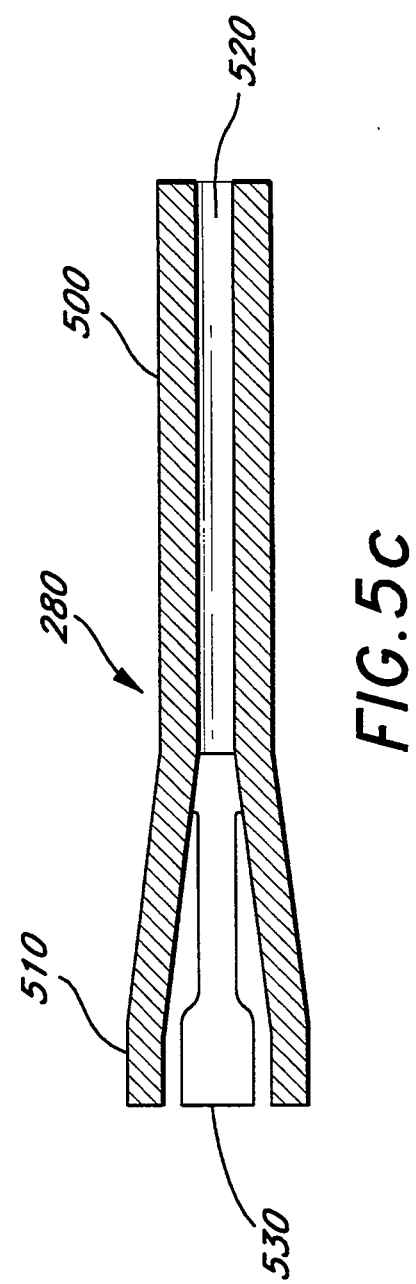

RECIPROCATING ARTHROSCOPIC SHAVER

This application is a continuation of application Ser. No. 08/106,275, filed Aug. 13, 1993, now abandoned.

BACKGROUND OF THE INVENTION

1. Field of the Invention

The present invention relates to the field of arthroscopic shaving devices.

2. Description of the Related Art

Generally, arthroscopic surgery is a method of surgery involving the use of catheter probes for viewing and operating on an internal portion of the body. Arthroscopic surgery may be employed, for example, to remove loose or damaged cartilage, or to shave off bone spurs.

Over the past several years, arthroscopic surgery has become a popular method for removing diseased or damaged tissue from intra-articular regions of the body, such as knee and shoulder joints. In particular, arthroscopic surgery has exhibited many advantages over other invasive surgical procedures due to the smaller incisions which are required to perform arthroscopic surgery. Thus, in applications such as sports medicine, where a quick recovery time is of utmost importance, arthroscopic surgery is highly desirable.

A variety of arthroscopic shaving and cutting devices have been developed to perform arthroscopic surgery. For example, one prior device includes a protruding saw-like member at the end of a catheter probe. The saw-like member is rapidly vibrated so that tissue or bone which comes into contact with the member is severed or dissected. This device, however, has a disadvantage in that the protrusion of the saw-like member generally produces sloppy cutting action. Furthermore, in the event of a breakdown or fragmentation of the saw-like member, the fragments of the saw-like member could disperse and remain in the tissue thereby creating more problems.

Another prior device includes a elongate hollow tubing in which is disposed a cutting or shaving blade. A revolving driving member rotates the cutting blade adjacent to a window in the tubing so that tissue or bone which enter into the window are cut off. Such devices provide cleaner cutting action and overcome certain disadvantages of the previously mentioned system, however, a rotating cutting blade usually necessitates a rigid revolving driving member as well as a rigid external tube. With these devices, it is relatively difficult to reach damaged tissue and bone in tight joints such as at the back of the knee, where a high proportion of injuries occur.

SUMMARY OF THE INVENTION

The present invention is an improved arthroscopic shaver especially adapted for overcoming the problems associated with prior art shavers. In particular, the present invention provides an arthroscopic shaver which provides the surgeon with (i) access to areas of the body which are difficult to reach, (ii) a "clean" cut of the body tissue so as to leave only a minimal amount of tissue particles after the shaving operation, and (iii) a suction force ample for quickly and efficiently removing any remaining debris from the situs of the surgery.

In its preferred embodiment, the cutting action of the shaver is provided by reciprocating movement of a first moving cutter blade across a juxtaposed second stationary cutter blade at the distal end of the shaver. This reciprocating scissors action enables the cutter to function as a side cutter within a cutting window located at the extreme distal ends of a slender column or tube. This tube advantageously includes a segment proximate its distal end which is bent with respect to the axis of the remainder of the column. The bent column of this invention facilitates entry of the proximal cutting window to places within the human body which are very difficult, if not impossible, to reach with contemporary arthroscopic cutting devices. In addition, the reciprocating motion of the cutter blade across the cutting window provides for a very clean cutting operation in which bone and tissue particles are minimal.

An additional significant feature of the invention is to provide a strong suction force through the cutting window to suck up any debris at the situs of the cutting operation. The suction force is advantageously provided by an external vacuum source and, in the preferred embodiment, also by a flapper valve physically connected to the reciprocating driver member.

A further feature of the invention contemplates the use of an end-cutting member, which is supported substantially within the tube portion of the shaver housing, extends from the extreme distal tip of the shaver tube. The end-cutting member includes a movable tongue and a fixed base portion which are coupled by a rail and groove guide assembly.

BRIEF DESCRIPTION OF THE DRAWINGS

FIG. 2e is an enlarged cross-sectional view of the end-cutting embodiment of the apparatus of the present invention, which shows the end-cutting member at the extreme distal tip of the tube portion of the shaver housing.

FIG. 3 is an enlarged perspective view of the cutting blade shown in FIGS. 2a–2d;

FIG. 3a is a side elevational cross-sectional view of the cutting blade along the line 3a—3a in FIG. 3;

FIG. 3b is a cross-sectional view of the cutting blade along the line 3b—3b of FIG. 3a;

FIG. 3c is a front view of the cutting blade;

FIG. 3d is a front view of an alternative embodiment of the cutting blade, wherein the channels are broadened to facilitate suction.

FIG. 5a is a side elevational view of the flapper valve employed in a preferred embodiment of the invention;

FIG. 5b is a front view of the flapper valve depicted in FIG. 5a; and

FIG. 5c is a side cross-sectional view taken along the line 5c—5c of the flapper valve depicted in FIG. 5a.

DETAILED DESCRIPTION OF THE INVENTION

A. Overall Configuration

Figure 1:
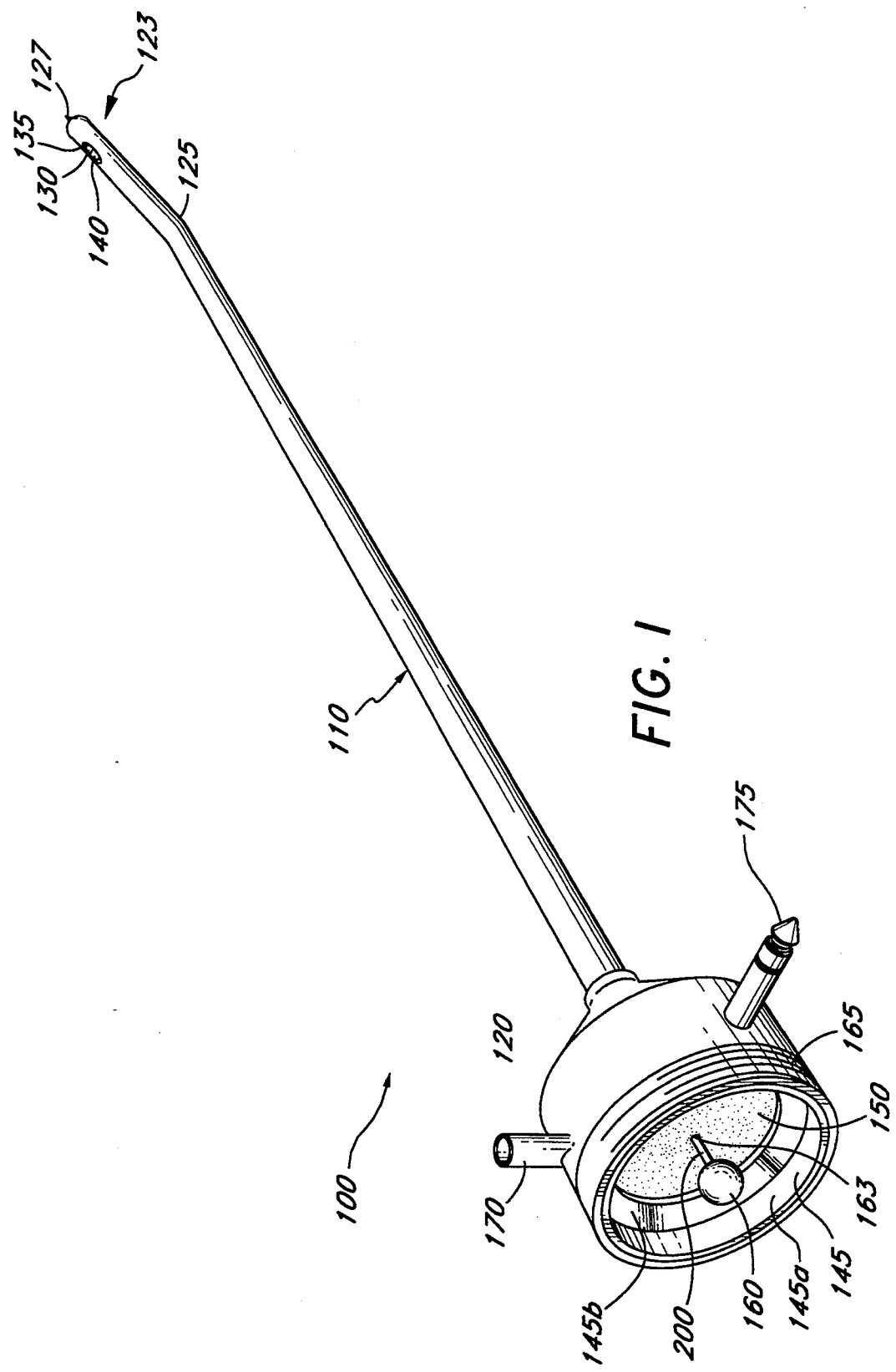
FIG. 1 is a perspective view of a side-cutting embodiment of the arthroscopic shaving apparatus of the present invention.

A side-cutting arthroscopic shaving device 100 constructed in accordance with the invention is shown in FIG. 1. The shaving device 100 includes an elongated hollow column or tube 110 extending distally from a base member 120. In one embodiment of the invention, the elongate tube 110 is formed as a separate member and attached to the base 120 by soldering, brazing, threaded engagement, or other connecting means known in the art. In an alternate embodiment, the tube 110 may be integrally formed with the base 120 to form a single, continuous housing.

As will be appreciated by one of ordinary skill in the art, the specific size and shape of the tube 110 will be determined by the specific application of the tube. The inner and outer diameters of the hollow tube 110 will also vary depending upon the specific application.

A significant feature of the present invention is that the shaving window can be positioned in very "hard to get to" places within the human body. Thus, tube 110 includes an angled distal region 123 which extends from the distal tip of the tube 110 to the angle 125 of the tube 110. The angled distal region 123 has been found to be particularly advantageous in applications where small or tight joints make it difficult to position the shaving device 100 at the proper cutting angle. The angle of extension of the distal region relative to the longitudinal axis of the proximal portion of tube 110 is typically within the range of about 10° to 30°, although certain special applications may call for an angle of extension on the order of 60°.

In the preferred embodiment of the invention, a tip 127 is formed at the extreme distal tip of the tube 110. Tip 127 is used to cauterize tissue at the distal tip of the tube 110. While tip 127 may be heated in any of a variety of known ways, RF radiation propagated through the tube 110 is advantageously used as the source of energy. In order to prevent unwanted RF discharge to tissue other than at the distal tip of the tube 110, the tube 110 is preferably coated with a non-conductive coating 128 which extends over substantially the whole tube 110 with the exception of the cauterizing tip 127. The coating may, for example, comprise a high purity nylon such as that used in conformed coating of circuit boards.

A shaving window or aperture 130 is formed within the distal region 123 of the tube 110. The aperture 130 may, for example, be formed by conventional stamping, cutting or grinding techniques, although any suitable manufacturing technique may be used. It is usually advantageous to form the aperture 130 as close to the distal tip of the tube 110 as possible; however, the actual distance of the aperture 130 from the tip of the tube 110 is typically determined by certain design constraints which will be discussed in detail with reference to FIGS. 2a–2d below.

The aperture 130 is sized to receive bits of damaged tissue for resection, and may be formed with various configurations (e.g., circular, oval, rectangular, etc.).

The aperture 130 has at least one cutting edge 135, which is shown in FIG. 1 to be formed at the distal edge of the aperture 130. However, it should be understood that the cutting edge may be formed at the distal edge, the proximal edge, or both the distal and proximal edges of the aperture 130, depending upon the desired direction of the cutting motion used in accordance with the shaving device 100. In one actual embodiment, both the distal and proximal edges are formed so that both of these edges could be used as the cutting edge, although, generally, only one of the proximal or distal edges is used.

Figure 2A:
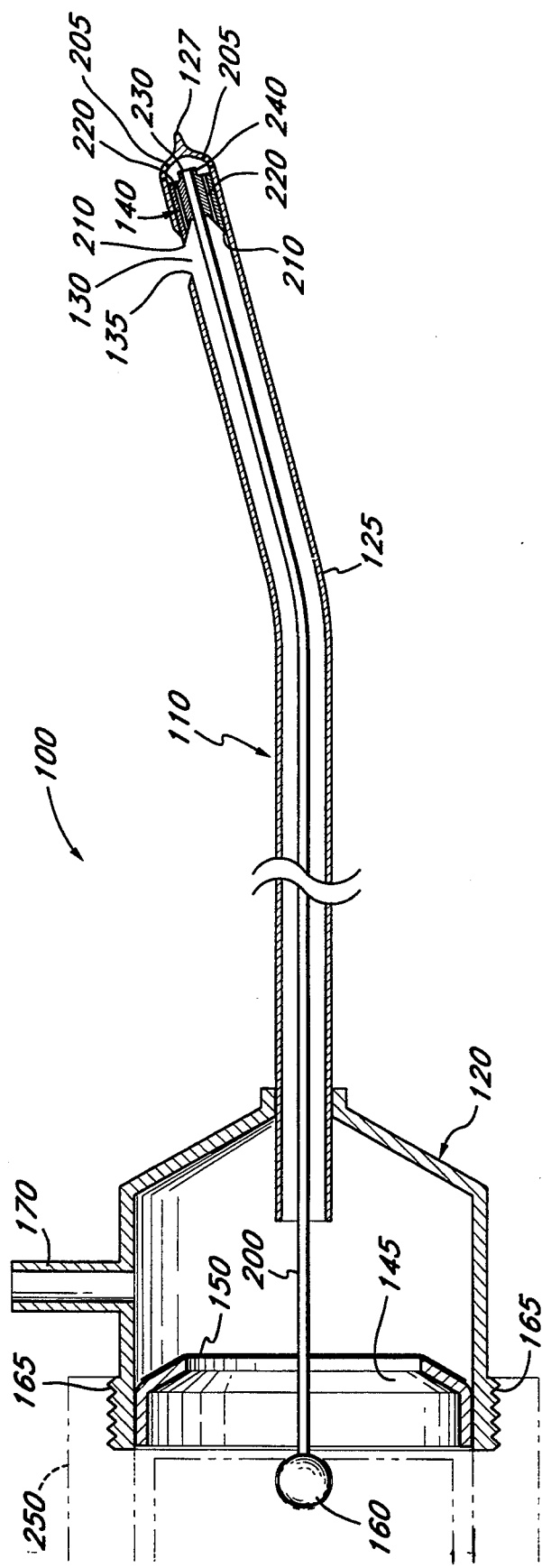
FIGS. 2a and 2b are enlarged cross-sectional elevational views of a first side-cutting embodiment of the apparatus of the present invention which show the internal components of the invention when the cutting motion of the blade is in the proximal direction.

Referring to FIGS. 1 and 2a, the base 120 in the illustrated embodiment is generally tubular with a conical distal wall. However, it will be readily apparent to one of ordinary skill in the art that the base 120 may be configured in a variety of ways in order to facilitate handling and manageability of the shaving device 100. The distal end of the base 120 connects to the tube 110 and the proximal end of the base 120 includes a diaphragm support ring 145 which supports a moveable diaphragm 150. If the base 120 is manufactured separately from the tube 110, then the base 120 may be made of the same or a different material than the tube 110.

An electrical connector 175 of the "banana plug" variety or other electrical connector to fit the application is attached to the surface of the member 120 or near the proximal end of tube 110, by welding, soldering, threading or other means known in the art. The electrical connector provides a means to connect a source of RF or other electrical energy to the device 100.

The support ring 145 has a first component which is basically a segment of a cylindrical wall integral with a second component, which is basically a conical segment having a central circular opening open to a substantial portion of the front face of the diaphragm 150. The support ring 145 is preferably made of a durable and relatively rigid material and is configured to insert into the proximal end of the base 120. Support ring 145 can frictionally or threadably engage the interior surface of the base 120, and is advantageously secured by the use of conventional adhesives.

The diaphragm 150 is advantageously made from surgical grade silicon rubber or other durable elastic material and forms a fluid-tight seal at the proximal end of the base 120. In one embodiment, the diaphragm 150 is stretched over the face of both the cylindrical and conical surfaces of the support ring 145 and the diaphragm 150 and support ring 145 are inserted together into the rear end of the base 120 where they may be secured by means of epoxy adhesive or the like.

A coupling anchor 160 is a ball-shaped member adjacent to the diaphragm 150 and approximately at the center of the diaphragm 150. As shown in FIG. 2a, a connecting member 200 is attached at its proximal end to the ball 160 and extends through diaphragm 150, along the length of the tube 110, to the distal region 123 where the distal end of the driver connecting member 200 is attached to the cutting member 140. The anchor 160 and cutting member 140 are advantageously brazed onto the driver connecting member 200, although it will be understood that any of a variety of attachment means such as solder or adhesives may also be used as called for by the specific application. The function of the connecting member 200 is to transmit a reciprocating axial force from the anchor 160 to the cutting member 140.

In general, it is desirable to form the hole 163 in the diaphragm 150 so that the diameter of the hole is slightly smaller than the diameter of the driver connecting member 200. As a result, the diaphragm 150 must stretch to fit over the connecting member 200 so that a tight seal is formed between the diaphragm 150 and the connecting member 200.

The structure of the connecting member 200 will be determined by whether or not it is desired to effect cutting during motion in the proximal direction or during motion in the distal direction. For example, in the embodiment shown in FIGS. 2a and 2b, cutting occurs while the cutting member 140 is moving in the proximal direction. The connecting member 200 should then be substantially inelastic when axial tension is applied to the connecting member 200. In this case, the connecting member 200 will advantageously be a solid wire or a braided cable.

Figure 2B:
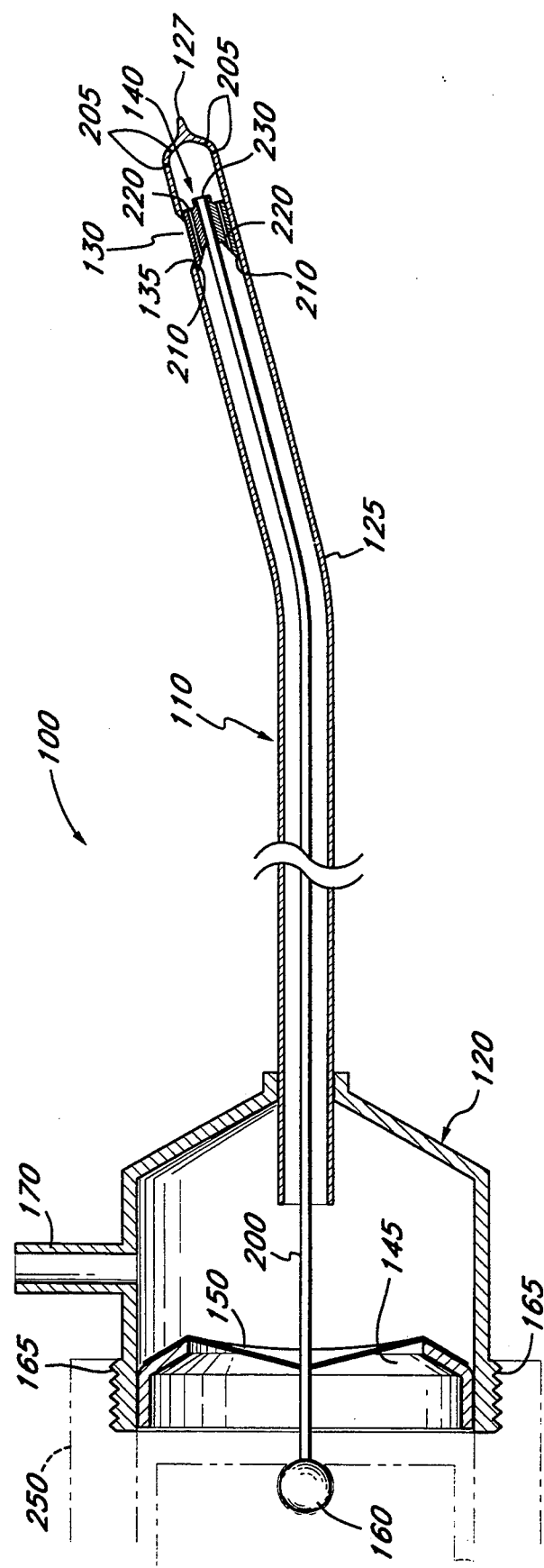
Figure 2C:
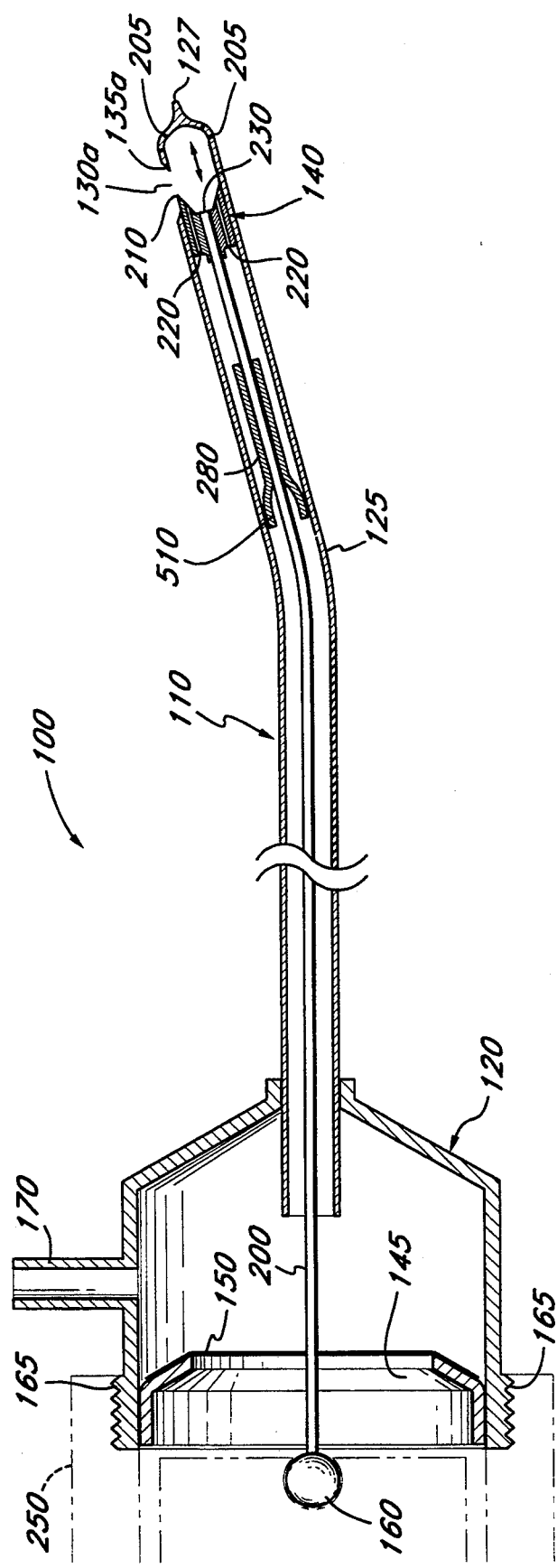
FIGS. 2c and 2d are enlarged cross-sectional elevational views of an alternate side-cutting embodiment of the apparatus of the present invention which show the major internal components of the invention when the cutting motion of the blade is in the distal direction.
Figure 2D:
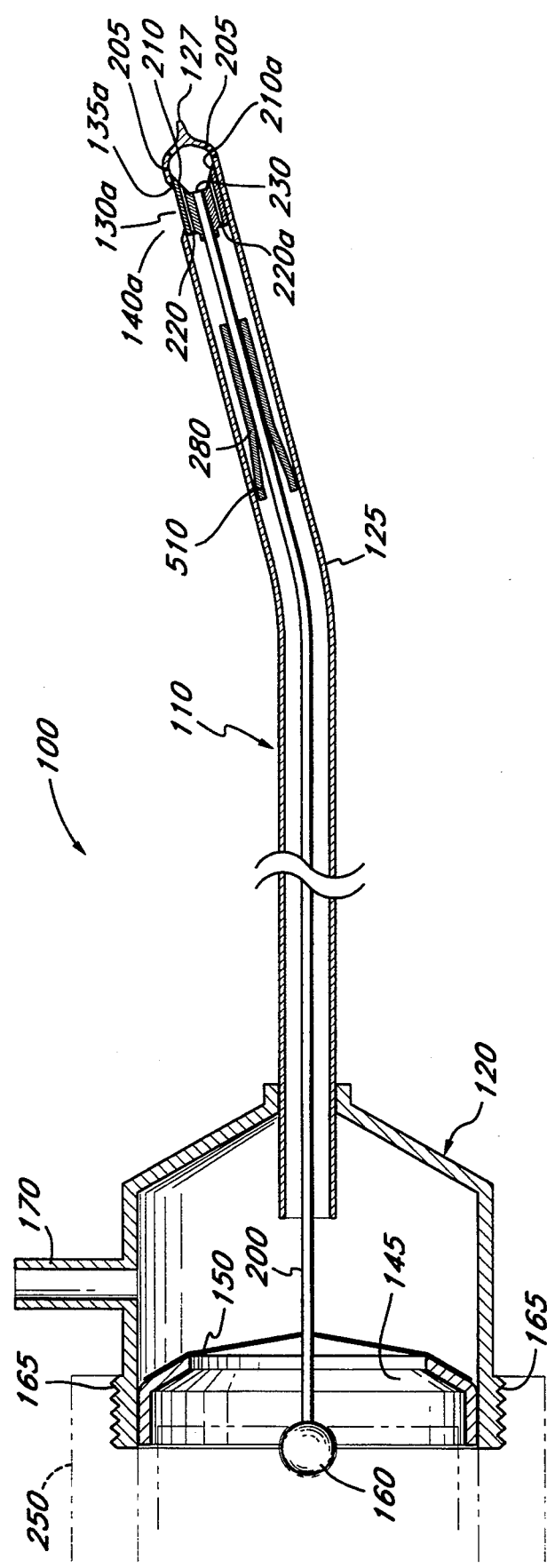

In the embodiment shown in FIGS. 2c and 2d, cutting occurs when a cutting member 140, which is supported substantially within the tube 110, is moving in the distal direction. The connecting member 200 should then exhibit sufficient column strength to drive the cutting member 140 when axial compression is applied to the driver connecting member 200. Driver connecting members 200 used in these applications advantageously comprise teflon or steel rods, for example, although it should be understood that a braided cable may also be employed provided that the characteristics of the cable are such to allow effective cutting of tissue or bone when the cutting member 140 is being pushed in a distal direction. In either case, it is desirable that the driver connecting member 200 be sufficiently flexible to easily bend at the angled distal end 125 of the tube 110. The driver connecting member 200 may also include, for example, an outer teflon sleeve to reduce friction between the connecting member 200 and the inside surface of the tube 110.

Threads 165 are preferably formed on the outside circumference of the base 120 near the diaphragm 150. The base 120 further includes a vacuum port 170 which extends from the side of the base 120. The vacuum port 170 is used to connect the interior of the tube 110 with a source of vacuum. In one embodiment, the vacuum port 170 is integrally formed with the base 120.

Also shown in FIGS. 2a–2d are a plurality of ventilation ports 205 which allow fluid to pass out of the distal tip of the tube 110. The ventilation ports 205 relieve pressure from building up at the distal end portion of the tube 110, and also prevent fluids at the distal end portion from becoming stagnant, and thereby inhibit clotting at the distal end of the tube 110.

The cutting member 140, attached at the distal end of the driver connecting member 200, includes cutting edges 210. The cutting member 140 is preferably made of a hard, machinable material so that the cutting edges 210 are durable and retain a sharp cutting edge. Cutting member 140 is configured to include through conduits or channels 220 which allow the passage of fluids and small particles to pass through the cutting member 140. The cutting member 140 further includes a receiving conduit 230 which is configured to receive and fixably engage the driver connecting member 200.

The distal end of connecting member 200 passes through the receiving conduit 230 of cutting member 140 and is attached at the other side. The diameter of the receiving conduit 230 of the cutting member 140 should be approximately equal or slightly greater than the diameter of the connecting member 200, so that the connecting member will easily pass through the receiving conduit 230. A shoulder portion 240 is advantageously formed on the distal side of the cutting member 140. The shoulder facilitates brazing of the driver connecting member 200 to the cutting member 140, or may also be used to facilitate other attachment means for securing the cutting member 140 and the driver connecting member 200. As a result, the driver connecting member 200 is securely attached to the cutting member 140 so that the cutting member 140 may be reciprocated longitudinally within the tube 110 by means of the connecting member 200. The features and configuration of the cutting member 140 will be described in greater detail below with reference to FIGS. 3a and 3b.

B. Operation of the Embodiment Shown in FIGS. 2a and 2b

In the embodiment shown in FIGS. 2a and 2b, the cutting edges 210 of the cutting member 140 face the proximal end of the tube 110, and the cutting edge 135 is formed at the proximal edge of the aperture 130 of tube 110 so that a shearing action between the edges 135 and 210 is effected when the cutting member 140 is moving in the proximal direction (shown in FIG. 2b).

FIG. 2b, in conjunction with FIG. 2a, depicts the general motion of the cutting member 140 within the shaving device 100. As shown in FIGS. 2a and 2b, a reciprocating driver adaptor 250 (shown in phantom, and discussed in greater detail with reference to FIG. 4 below) is affixed to the shaving device 100 such as by means of the threads 165. The coupling ball 160 is attached to the reciprocating driver adaptor 250 so that the ball 160 acts as a driver coupling member.

In a first position, shown in FIG. 2a, the diaphragm 150 is at rest and the cutting edge 210 of the cutting member 140 is spaced from the cutting edge 135 of the aperture 130. In a second position, shown in FIG. 2b, the reciprocating driver adaptor 250 has pulled on the ball 160 so that the driver connecting member 200, and thereby the cutting member 140, is axially translated in the proximal direction along the length of the tube 110. The distance which the cutting member 140 is pulled is sufficient to traverse the space between the cutting edge 210 and the cutting edge 135 in a scissor-like action. Loose cartilage, other joint tissue and the like which protrude into the aperture 130 are cut by the scissor action of the cutting edges 210 and 135. In order to optimize the scissor action of the cutting edges 210 and 135, it is advantageous for the cutting member 140 to fit snugly within the hollow tube 110, so that the inner diameter of the tube 110 is substantially equal to the outer diameter of the cutting member 140.

A significant feature of the present invention is that the scissor cutting action provides a smooth cut to minimize the formation of bone chips and tissue debris at the sites of the shaving operation. Another feature of the present invention is that it provides an arthroscopic shaver which automatically removes, during each cutting stroke, the debris formed. Thus, a suction force is continuously presented by the source of vacuum attached to part 170.

C. Construction and Operation of the Embodiment Shown in FIGS. 2c and 2d

FIGS. 2c and 2d are cross-sectional elevational views of the shaving device 100 which depict an embodiment of the invention wherein the cutting motion of the shaving device 100 is in the distal direction. The device shown in FIGS. 2c and 2d are substantially similar to that shown in FIGS. 2a and 2b with the exception that the cutting member 140 is facing in the distal direction and a flapper valve 280 is attached to the connecting member 200. Therefore, like elements are designated by like numbers.

In FIG. 2c, the reciprocating driver adaptor 250 is coupled to the ball 160 in a manner similar to that shown in FIGS. 2a and 2b above. In a first position, shown in FIG. 2c, the diaphragm 150 is at rest and the cutting edge 210 of the cutting member 140 is spaced from the cutting edge 135 of the aperture 130a. It should be noted that in the embodiment shown in FIG. 2c and 2d, the cutting edge 135a is formed on the distal edge of the aperture 130a.

In a second position shown in FIG. 2d, the reciprocating driver adaptor 250 applies force in the distal direction to the coupling ball 160 so that the driver connecting member 200, and thereby the cutting member 140, is pushed in the distal direction along the length of the tube 110. The distance which the cutting member 140 is pushed is sufficient to traverse the space between the cutting edge 210 and the cutting edge 135. Thus, loose cartilage, bone spurs and the like which protrude into the aperture 130a may be cut by the scissor action of the moving cutting edge 210 and stationary cutting edge 135.

D. Comparison of the Two Embodiments

In FIGS. 2c and 2d, the aperture 130a is located closer to the distal tip of the shaving device 100 than is aperture 130 in the embodiment shown in FIGS. 2a and 2b. This is due, in part, to the orientation of the cutting member 140 within the tube 110. The primary factors which determine the distance that the aperture 130 or 130a is spaced from the distal tip of the tube 110 in side-cutting applications include the size of the cutting member 140, and the stroke length of the reciprocating driver adaptor 250, however, these factors typically are not as important when the cutting member is facing in the distal direction as shown in FIGS. 2c and 2d. This is because the important consideration in most side-cutting applications of the shaving device 100 is that the cutting edge 210 be spaced a suitable distance from the cutting edge 135a in a first position to allow entry of tissue into the aperture 130a, and that the cutting member 140 traverse the distance between the cutting edge 210 and the cutting edge 135a in a second position to allow shaving of the tissue. The distance between the cutting edge 210 at the first position and the cutting edge 210 at the second position is typically equal to the stroke length of the cutting member 140.

In the embodiment shown in FIGS. 2a and 2b, the cutting member 140 faces in the proximal direction. The total distance that the distal end of the cutting member 140 extends beyond the cutting edge 135 is equal to the sum of the desired distance between the cutting edge 135 and the cutting edge 210, and the length of the cutting member 140. In order to determine the distance from the non-cutting edge of the aperture 130 and the distal tip of the tube 110, one merely subtracts the length of the aperture from the total distance that the distal end of the cutting member 140 extends beyond the cutting edge 135. In this manner the minimum distance between the distal tip of the tube 110 and the aperture 130 may be determined for side-cutting applications where the cutting member 140 is facing the proximal direction.

In the embodiment shown in FIGS. 2c and 2d, the body of the cutting member 140a, and the necessary spacing of the cutting edge 210 from the cutting edge 135a are both located on the proximal side of the cutting edge 135a. Therefore, the only consideration restricting the distance from the aperture 130a to the distal tip of the tube 110 is the requirement that the cutting edge 210 of the cutting member 140 be allowed to continue its stroke over and sufficiently beyond the cutting edge 135 so as to provide a clean shaving cut.

E. Operation of the Flapper Value 280

The flapper valve 280 shown in FIGS. 2c and 2d is advantageously used immediately after each shaving operation to increase the vacuum pull produced within the tube 110 so that tissue will more readily be drawn into the aperture 130a from the outside of the tube 110, and small bits of tissue will be pulled through the channels 220 onto the proximal side of the cutting member 140. The flapper valve 280 is configured so that when the cutting member 140 and the driver connecting member 200 are moving in the proximal direction toward the vacuum part 170 within the proximal end of tube 110, as illustrated in FIG. 2c, the flapper valve 280 opens and the edges of the flaps 510 touch the internal surface of the tube 110. The valve flaps 510 are sufficiently rigid in the open position so that as the connecting member 200 continues to be drawn in the proximal direction a suction force is formed on the distal side of the flap 280. When the cutting member 140 and the connecting member 200 are moved in the distal direction, however, the valve flap 280 moves inward so that tissue resected during the prior cutting stroke of the cutting member 140 is not retarded by the valve flap 280 and can pass by it toward the vacuum port 170.

The suction provided by the open flaps 510 advantageously increases the power of the vacuum provided by means of the vacuum port 170. Thus, tissue is more readily drawn into the aperture 130a.

It has been found that the valve flap 280 is quite advantageous when used in the embodiment of the invention shown in FIGS. 2c and 2d, however, it will be understood by one skilled in the art that the valve flap 280 may be advantageous in other embodiments of the invention described herein.

F. The Cutting Member 140

The cutting member 140 is shown in detail in FIGS. 3-3d. As shown, the cutting member 140 is generally cylindrical in shape and has a frusto-conical opening 290 (seen most clearly in the side cross-sectional view of FIG. 3a) which may, for example, be bored into the cutting member 140 by means of conventional machining and manufacturing processes so that a sharp edge is provided as the cutting edge 210. It will be appreciated, however, by one skilled in the art, that a variety of manufacturing processes may be used so long as the proper dimensions and sharpness of the cutting edge of the cutting member 140 is achieved.

The frusto-conical opening in the cutting member 140 terminates at a flat interior shoulder portion 300. The receiving conduit 230 continues from the interior shoulder portion 300 through the remainder of the cutting member 140. At the end of the cutting member 140 the shoulder portion 240 is formed.

As discussed above, a plurality of the channels 220 are also formed through the cutting member 140. It has been found that the incorporation of the channels 220 is advantageous in certain applications since it prevents a difference in fluid pressure from being formed on either side of the cutting member 140 thereby reducing resistance during the cutting stroke. In addition, channels 220 allow the fluid and small pieces of tissue or bone to be irrigated out of the tube 110 by means of the vacuum port 170.

An additional advantage of the channels 220 is provided when the cutting member 140 is located within the embodiment of FIGS. 2c and 2d such that its cutting edge faces in the distal direction. Channels 220 facilitate the formation of a vacuum on the distal side of the cutting member 140 when suction is formed on the proximal side of the cutting member 140 by means of the vacuum port 170 and the flapper valve 280. Bone and tissue particles are drawn into the aperture 130 by the vacuum and, as a result, the bone and flesh tissue are more easily cut when the cutting edge 210 is drawn over the cutting edge 135a.

In one embodiment of the cutting member 140, eight circular channels 220 are radially and symmetrically situated about the longitudinal axis (i.e., the axis which extends through the receiving conduit 230) of the cutting member 140, although it should be understood that the number, shape, and position of the channels 220 may vary from application to application. The channels 220 may be formed by drilling or other conventional machining process, although, again, it should be noted that the means of producing the channels 220 may vary considerably as dictated by the particular application or available manufacturing means.

In a second embodiment, shown in FIG. 3d, four symmetrically positioned channels 222 are wider than the channels 220 so as to facilitate suction. The channels 222 are particularly advantageous for use when larger pieces of tissue are cut by the cutting blade 140 since the widened channels 222 are not easily clogged.

G. The End Cutting Blade 600

Figure 6A:
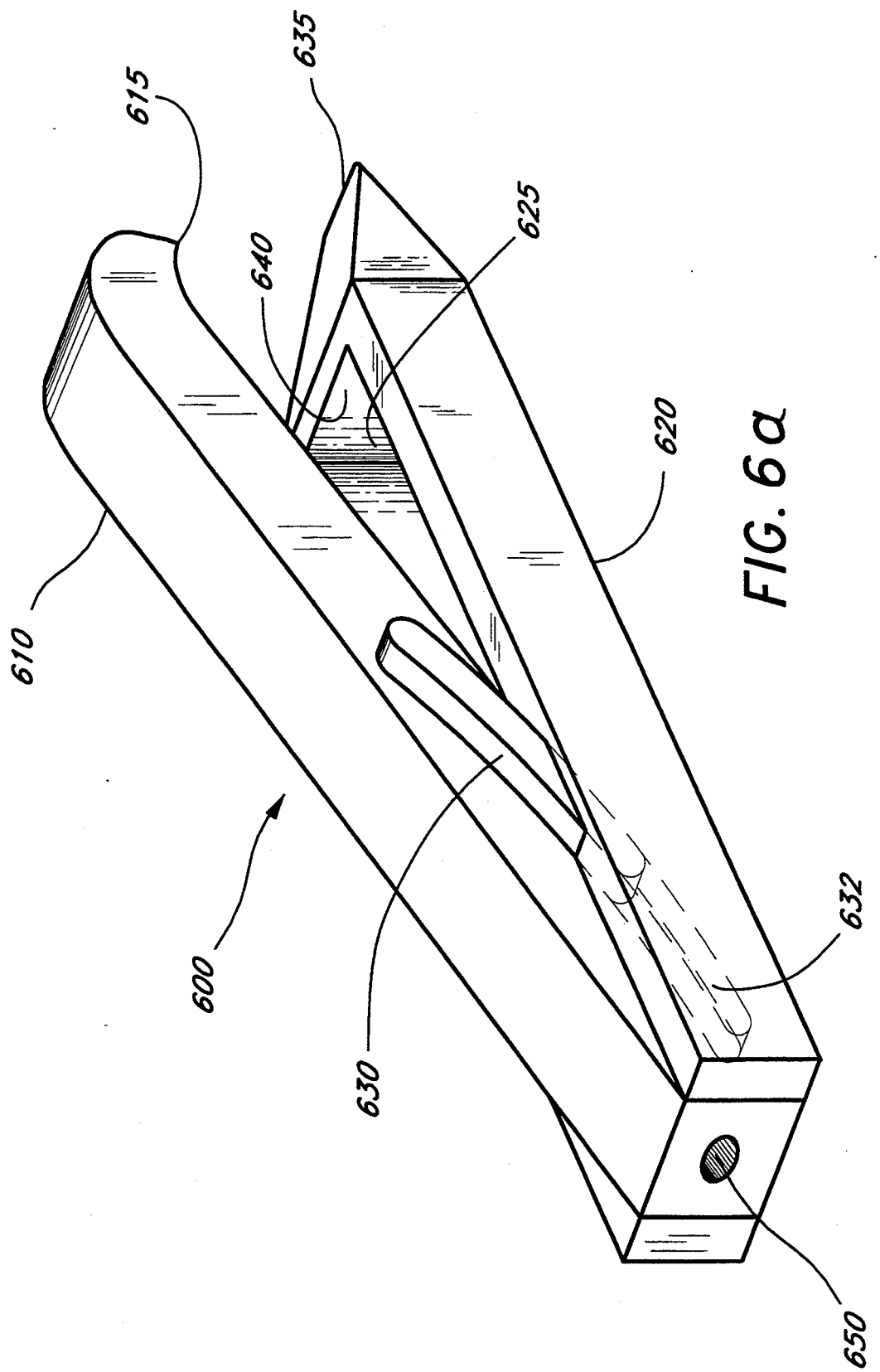
FIGS. 6a–6c are perspective, side elevational, and front views respectively of an alternative end-cutting embodiment of the cutting apparatus used in accordance with the present invention.
Figure 6C:
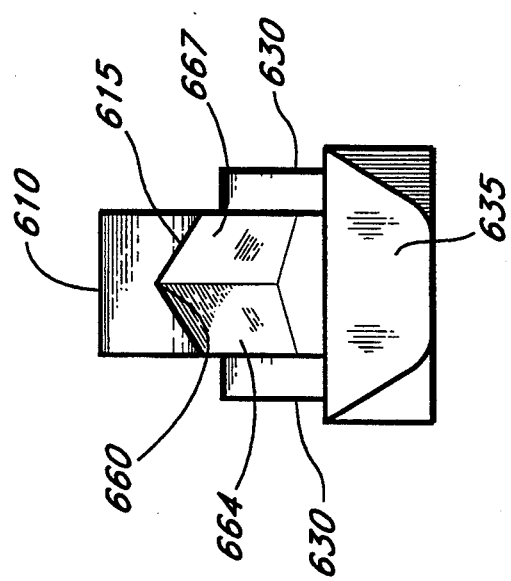
Figure 6B:
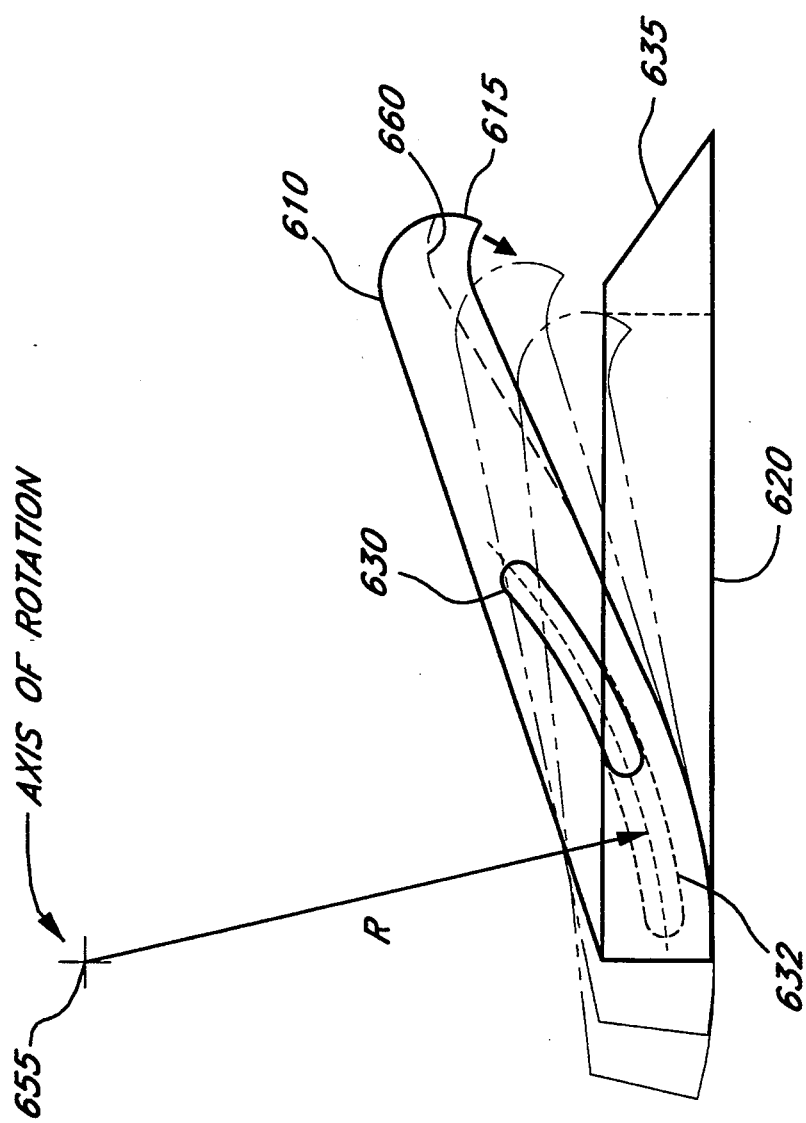

FIGS. 6a–6c show an alternative embodiment of the cutting apparatus employed in accordance with the present invention. In certain arthroscopic shaving applications it is desirable to use an end-cutting member such as an end-cutting blade 600 shown in perspective in FIG. 6a. End-cutting arthroscopic shavers are especially advantageous for use in tight or small spaces such as certain joints (e.g., the back of the knee). An end-cutting embodiment of the shaver constructed in accordance with the present invention is shown in FIG. 2e. Rather than having an aperture formed in the side of the tube 110, an arthroscopic shaver for use with the end-cutting blade 600 has an aperture formed at the very end of the distal region 123 (i.e., in place of the cauterizing tip 127). As can be seen in FIG. 2e, the end-cutting blade 600 is supported substantially within the tube 110 by an integrally formed attachment joint 601, in one embodiment (which may vary in shape and size according to the desired attachment means).

Because the aperture is formed at the tip of the distal region 123, the edge of the aperture in the end-cutting embodiment cannot be used to provide a shearing edge (as does the edge 135 of the aperture 130 shown in FIGS. 2a–2d). Therefore, the end-cutter 600 has a cutting tongue portion 610 which engages with a base portion 620 having a groove 625 formed therein. The cutting tongue 610 slides snugly into the groove 625 to provide a shearing action as will be described in greater detail below.

As shown in FIGS. 6a–6c, the tongue 610 includes a sharp front edge 615, as well as a pair of guide rails 630 which slidably engage with a pair of matching slots 632 (shown in hidden lines) formed within the base portion 620. The base 620 includes a shovel nose 635 which aids in pushing tissue up towards the cutting tongue 610. The groove 625 includes a front face 640 which acts as a shearing surface against which the cutting tongue 610 is counterposed. The tongue 610 further includes an attachment receptacle 650, formed in the proximal end of the tongue portion 610, which is used to retain the connecting member 200 (FIGS. 2a–2d).

The base portion 620 is secured within the interior of the tube 110 so that the base 620 is substantially immobile relative to the tube 110. The reciprocating motion of the connecting member 200 causes the attached cutting tongue portion 610 to slide in and out of the groove 625, as shown in phantom in FIG. 6b. The motion of the tongue 610 is determined by the guide rails 630 as the guide rails 630 slide within the slots 632. In the embodiment shown, the slots 632 and engaging guide rails 630 are circular in curvature and have a center radius of curvature R as measured from an imaginary axis of rotation (indicated as extending perpendicular to the surface of the page), and a width W. In one embodiment, R=0.33 in, and W=0.012 in. As the guide rails 630 slide along the slots 632, towards the proximal end of the base portion 620, the cutting tongue 610 is drawn downward and in the proximal direction, as shown by the arrow in FIG. 6b. The cutting tongue includes a V-shaped notch 660, having interior surfaces 664, 667, which aids in catching and drawing tissue to be cut.

In one actual embodiment, the end-cutter 600 is 0.25 in long, and 0.1 in wide. The end-cutter 600 is preferably made from a hardenable grade stainless steel such as 17-4 PH steel.

When the end-cutting blade 600 is used to cut tissue, the physician pushes the tip of the shaver 100 against the tissue. The shovel nose 635 lifts the tissue up to the cutting tongue 610. As the cutting tongue 610 reciprocates, the notch 660 catches the tissue so that the tissue is drawn inward by the tongue 610 during reciprocation in the proximal direction. The tissue is then caught between the tongue 610 and the front surface 640 of the groove 625, and subsequently cut by the shearing action between the sharp front edge 615 of the tongue 610 and the front surface 640 of the groove 625. The cut tissue is then pulled out through the bottom of the groove 625 by means of the suction provided within the tube 110.

H. The Reciprocation Drive Adaptor

Figure 4:
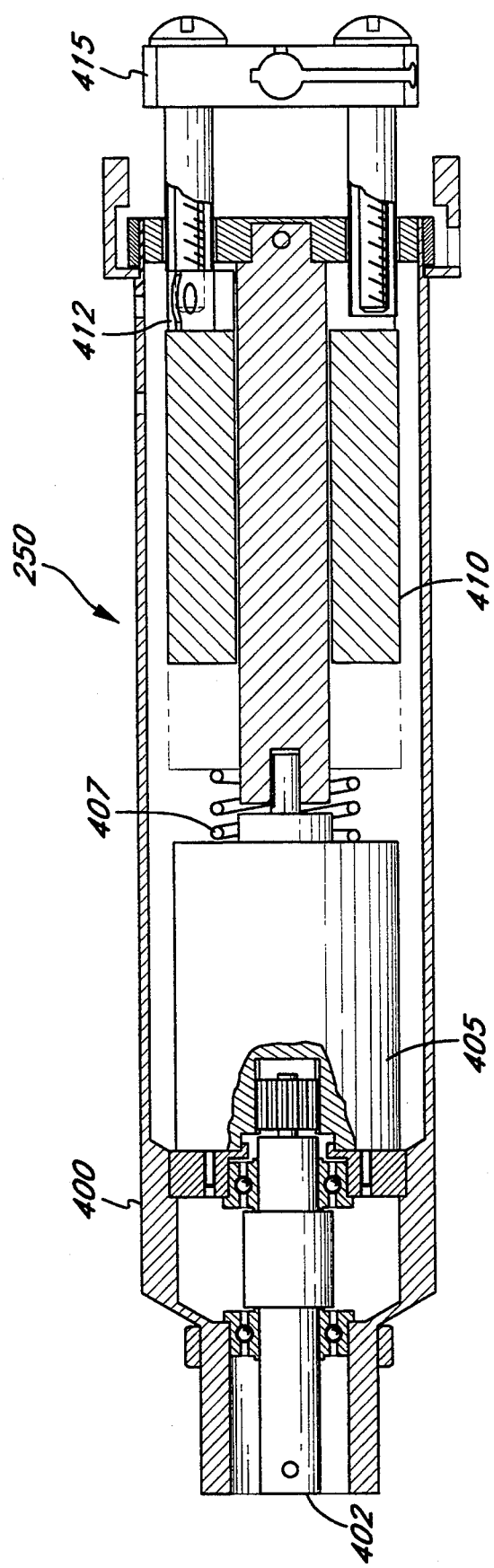
FIG. 4 is a schematic diagram showing the major structural elements of a rotational-to-reciprocating adaptor used with the arthroscopic shaver of the present invention.

FIG. 4 is a schematic cross-sectional diagram of the reciprocating driver adaptor 250. The adaptor 250 converts the motion of a rotational driver (not shown) into reciprocating motion. Devices which convert rotational motion to translational, or reciprocating, motion are well known.

The major structural elements of the adaptor 250 are shown in FIG. 4. A main housing 400 encloses a rotational input coupler 402 connected to a speed reducer planetary gear set 405. The gear set 405 attaches to a ball reverser 410, and a compression spring 407 is interposed between the ball reverser 410 and the gear set 405. The ball reverser 410 connects to an anti-rotation plate 412, which in turn connects with a lock assembly 415. The lock assembly 415 is in turn attached to show FIGS. 2a, 2b, 2c and 2d. The major structural elements of the adaptor 250 are commercially available devices as listed below.

In operation, the rotational coupler 402 is attached to the driving shaft member of a conventional rotational driver. The coupler 402 transmits the rotational force exerted by the rotational driver to the gear set 405. The gear set 405 comprises a set of step down gears so that, in one embodiment, a rotating member which has a rotational speed equal to 1/16th of the original driver shaft speed is provided at the output of the gear set 405.

The rotating member output from the gear set 405 connects to the ball reverser 410. The ball reverser 410 converts the rotational motion of the rotating member output from the gear set 405 into a reciprocating motion. The reciprocating motion is transmitted to the lock assembly 415 so that the lock assembly reciprocates periodically with a stroke length in one embodiment of 0.44 inches. The lock assembly 415 fixably retains the coupling ball 160 to produce the desired reciprocating motion in the arthroscopic shaver 100.

I. The Flapper Valve 280

FIGS. 5a–5c show the flapper valve 280 in greater detail. This valve 280 generally comprises an extended shaft portion 500 and a flexible end flaps 510. The shaft portion 500 has a generally cylindrical configuration and includes a passage 520. The passage 520 is configured to receive the connecting member 200 and has an internal diameter approximately equal to the diameter of the member 200 so that the valve 280 may be fastened to the connecting member 200 as shown in FIGS. 2c and 2d. The end flaps 510 preferably comprise four flexible paddles 530 which fold to decrease fluid resistance when the flap 280 is moved rapidly in the distal direction, i.e., in the direction of the shaft portion 500, and which extend to increase fluid resistance when the flap 280 is moved rapidly in the proximal direction, i.e., in the direction of the end portion 510. To this end, the flap 280 may be constructed from a material such as polyethylene, although it will be appreciated that other suitable materials may also be used.

J. Specifications of Exemplary Embodiments of the Arthroscopic Shaver

By way of specific example, an exemplary embodiment shown in FIGS. 2c and 2d was constructed in accordance with the following specifications:

| Part No. | Part Name | Size | Material | Source |
|---|---|---|---|---|
| 110 | Hollow tube | Length = 5 inches<br>Inner Diameter = 0.094 inches<br>Outer Diameter = 0.120 inches<br>Wall Thickness = .026 inches | 304 grade stainless steel, full hard | Tubesales Los Angeles, CA |
| 123 | Angled Distal Segment | Length = 1.05 inches<br>Scope of Extension = 15° | | |
| 128 | Non-Conductive Coating | Thickness = .003 inches | Parylene | Novatran Corp., Montclair, CA |
| 130 | Aperture | Diameter = 0.094 inches | | |
| 140 | Cutting Member | | 17-4 PH steel | Trye Steel Santa Fe Springs, CA |
| 145 | Support Ring | | 303 stainless steel | Trye Steel Santa Fe Springs, CA |
| 150 | Diaphragm | Diameter = 1.36 inches<br>Thickness = 5 to 10 mils | Surgical Grade Silicon rubber | Hygenic Corp., Akron, OH |
| 163 | Hole in Diaphragm | Diameter = 16 mils | | |
| 200 | Driver Connecting Member | Diameter = 20 mils | Solid stainless steel (316 grade) | Cablestrand Corp. Long Beach, CA |
| 220 | Channels | Diameter = 0.008 inches | | |
| 280 | Flapper Valve | | Polyethylene | Harrington Plastics Los Angeles, CA |
| 290 | Frusto-conical Opening Rotational Driver for Driver Adaptor | Included angle = 60° | 17-4 pH Steel | |
| 402 | Rotational Input | input rpm = 4800 | | |
| 405 | Speed Reducer | 16:1 gear ratio | | |
| 410 | Ball Reverser | 0.44 inch strobe per revolution of the rotational driver<br>300 strokes per minute | | Flennor, Inc., 139 Allan Dr., Ridgefield, CT 06877 |

It will be appreciated that the shavers of both embodiments of this invention may be constructed in a number of different embodiments and sizes. Representative ranges of various parts of the invention are:

| Part No. | Part Name | Range of Sizes |
|---|---|---|
| 110 | Hollow Tube | Length = 4 to 7 inches<br>Outer Diameter = .1 to .2 inches |
| 123 | Angled Distal Segment | Length = .5 to 1.5 inches<br>Angle of Extension = 10° to 60° |
| 130 | Aperture | Diameter = .1 to .24 inches |
| 220 | Channels | Diameter = .008 to .050 inches may be: |
| 290 | Frusto-conical Opening | Included angle = 45° to 60° |
| 402 | Rotational Input | 1600 rpm to 6400 rpm |
| 410 | Ball Reverser | .2 inch strokes to .6 inch strokes per revolution of the rotational drive; 100 to 400 strokes per minute |

The present invention may be further embodied in other forms and specifications without departing from its spirit or essential characteristics. Thus, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

I claim:

1. An arthroscopic shaving device comprising:
   an elongated housing extending substantially along a longitudinal axis, said housing including a distal portion having a distal portion axis which is inclined relative to said longitudinal axis, said housing further including an aperture formed within said distal portion;
   a cutting member disposed within said housing;
   a connector which is attached to said cutting member at a first end and is attached to a driver coupling member at a second end so that said connector extends through said housing, said connector being configured to produce movement of said cutting member longitudinally within said distal portion of said housing so that said cutting member traverses at least a portion of said aperture; and an adaptor assembly having an attachment means to engage a rotary arthroscopic shaver power driver at one end, wherein said adapter assembly converts rotary motion to reciprocating motion.

2. An arthroscopic shaver as defined in claim 1, wherein said axis of said distal portion is inclined to said longitudinal axis of the housing in the range of 10° to 60°.

3. An arthroscopic shaver as defined in claim 1, wherein said distal portion can be bent relative to said longitudinal axis of said housing as required by a surgeon or other operating room personnel to fit a particular surgical application.

4. An arthroscopic shaver as defined in claim 1, wherein said aperture is formed on the side of said distal portion.

5. An arthroscopic shaver as defined in claim 1, wherein said aperture is formed at the end of said distal portion, thereby allowing for end-cutting using said shaver.

6. An arthroscopic shaver as defined in claim 5, wherein said cutting member comprises a tongue and groove assembly wherein a tongue portion acts a moveable cutting blade having its motion determined by a groove formed in a fixed base section of said tongue and groove assembly.

7. An arthroscopic shaver as defined in claim 6, wherein said tongue portion has an inverted V-notch to facilitate cutting of tissue.

8. An arthroscopic shaver as defined in claim 1, wherein said cutting member has material removed from its center so as to provide maximum flow area to an irrigation channel through said cutting member but still providing sufficient structural integrity to said cutting member while providing an attachment point for said connector to drive said cutting member.

9. An arthroscopic shaver as defined in claim 8, wherein said housing has a substantially hollow interior which acts as an irrigation channel, and wherein said irrigation channel is separated from said driver coupling member by a fluid tight elastic membrane.

11. An arthroscopic shaver as defined in claim 9 or 10, wherein a vacuum port is provided near the proximal end of said irrigation channel for connection to a suitable vacuum source for drawing cutting debris and fluid.

10. An arthroscopic shaver as defined in claim 8, wherein said housing has a substantially hollow interior which acts as an irrigation channel, and wherein said irrigation channel is separated from said driver coupling member by a fluid tight fixed Oring packaging seal through which said connector slides.

12. An arthroscopic shaver as defined in claim 1, wherein said housing is formed to have an enclosed circular cross-section and a substantially constant wall thickness throughout the length of the housing.

13. An arthroscopic shaver as defined in claim 1, wherein a flapper valve is attached to said connector so as to provide increased suction within said irrigation channel.

14. An arthroscopic shaver as defined in claim 1, wherein said connector comprises a flexible cable fabricated of a single multi-strand stainless steel wire.

15. An arthroscopic shaver as defined in claim 1, wherein said connector comprises a flexible cable fabricated of a durable plastic.

16. An arthroscopic shaving device comprising:

an elongated housing extending substantially along a longitudinal axis, said housing including a distal portion having a distal portion axis which is inclined relative to said longitudinal axis, said housing further including an aperture formed within said distal portion, said housing further including an outer surface, said outer surface being covered with a non-conductive material which prevents discharge of radio frequency electrical energy except at the distal portion of said housing thereby facilitating electro-cautery;

a cutting member disposed within said housing;

a connector which is attached to said cutting member at a first end and is attached to a driver coupling member at a second end so that said connector extends through said housing, said connector being configured to produce movement of said cutting member longitudinally within said distal portion of said housing so that said cutting member traverses at least a portion of said aperture.

17. An arthroscopic shaving device comprising:

an elongated housing extending substantially along a longitudinal axis, said housing including a distal portion having a distal portion axis which is inclined relative to said longitudinal axis, said housing further including an aperture formed within said distal portion;

a cutting member disposed within said housing;

a connector which is attached to said cutting member at a first end and is attached to a driver coupling member at a second end so that said connector extends through said housing, said connector being configured to produce movement of said cutting member longitudinally within said distal portion of said housing so that said cutting member traverses at least a portion of said aperture; and a flapper valve attached to said connected so as to provide increased suction within said irrigation channel, said flapper valve being molded in a single piece of plastic such as polyethylene with two or more paddles attached to flexible arms, said arms enabling the paddles to move outward when the flapper valve is propelled in one direction, and inward when propelled in the opposite direction, and wherein said flapper valve has an increased cross-sectional area when said paddles move outward than when said paddles move inward.

18. An arthroscopic shaving device comprising:

an elongated housing extending substantially along a longitudinal axis, said housing including a distal portion having a distal portion axis which is inclined relative to said longitudinal axis, said housing further including an aperture formed at the end of said distal portion, thereby allowing for end-cutting using said shaver;

a cutting member disposed within said housing, said cutting member comprising a tongue and groove assembly wherein a tongue portion acts as a movable cutting blade having its motion determined by a groove formed in a fixed base section of said tongue and groove assembly, said tongue portion having an inverted V-notch to facilitate cutting of tissue;

a connector which is attached to said cutting member at a first end and is attached to a driver coupling member at a second end so that said connector extends through said housing, said connector being configured to produce movement of said cutting member longitudinally within said distal portion of said housing so that said cutting member traverses at least a portion of said aperture.

* * * * *